US009640449B2

(12) United States Patent
Goodwin et al.

(10) Patent No.: US 9,640,449 B2
(45) Date of Patent: May 2, 2017

(54) AUTOMATED INLINE INSPECTION OF WAFER EDGE STRAIN PROFILES USING RAPID PHOTOREFLECTANCE SPECTROSCOPY

(71) Applicant: KLA-Tencor Corporation, Milpitas, CA (US)

(72) Inventors: Timothy Goodwin, Mountain View, CA (US); Lena Nicolaides, Castro Valley, CA (US); Mohan Mahadevan, Livermore, CA (US); Paul Horn, Milpitas, CA (US); Shifang Li, Pleasanton, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 38 days.

(21) Appl. No.: 14/688,739

(22) Filed: Apr. 16, 2015

(65) Prior Publication Data

US 2015/0371910 A1 Dec. 24, 2015

Related U.S. Application Data

(60) Provisional application No. 61/982,196, filed on Apr. 21, 2014, provisional application No. 62/057,126, filed on Sep. 29, 2014.

(51) Int. Cl.
*G01N 21/88* (2006.01)
*G01N 21/95* (2006.01)
(Continued)

(52) U.S. Cl.
CPC .............. *H01L 22/24* (2013.01); *G01B 11/16* (2013.01); *G01N 21/8806* (2013.01);
(Continued)

(58) Field of Classification Search
CPC .......... G01N 21/8806; G01N 21/9503; G01N 21/95; G01N 2201/0611; H01L 22/12; H01L 22/24; G01B 11/16
(Continued)

(56) References Cited

U.S. PATENT DOCUMENTS 7,016,044 B2 3/2006 Murtagh et al.
7,616,307 B2 11/2009 Murtagh et al.
(Continued)

FOREIGN PATENT DOCUMENTS

IE 83595 B1 9/2004
IE 83734 B1 12/2004
(Continued)

OTHER PUBLICATIONS

PCT Search Report for International Application No. PCT/US2015/026775 dated Aug. 26, 2015.
(Continued)

*Primary Examiner* — Sang Nguyen
(74) *Attorney, Agent, or Firm* — Suiter Swantz pc llo (57) ABSTRACT

Photoreflectance spectroscopy is used to measure strain at or near the edge of a wafer in a production process. The strain measurement is used to anticipate defects and make prospective corrections in later stages of the production process. Strain measurements are used to associate various production steps with defects to enhance later production processes.

21 Claims, 7 Drawing Sheets (51) Int. Cl.
*H01L 21/66* (2006.01)
*G01B 11/16* (2006.01)

(52) U.S. Cl.
CPC ......... *G01N 21/95* (2013.01); *G01N 21/9503* (2013.01); *H01L 22/12* (2013.01); *G01N 2201/06113* (2013.01)

(58) Field of Classification Search
USPC .................................. 356/32, 447, 364, 365
See application file for complete search history.

(56) References Cited

U.S. PATENT DOCUMENTS

| | | | |
|---|---|---|---|
| 7,616,308 B2 | 11/2009 | Murtagh et al. | |
| 7,623,228 B1 | 11/2009 | Muckenhirn | |
| 7,659,979 B2* | 2/2010 | Murtagh | G01N 21/1717 356/237.2 |
| 7,755,752 B1 | 7/2010 | Salnik et al. | |
| 7,773,212 B1* | 8/2010 | Wolters | G01N 21/9501 356/237.4 |
| 2003/0053039 A1* | 3/2003 | Nagai | G03F 7/2028 355/53 |
| 2003/0098704 A1 | 5/2003 | Du-Nour et al. | |
| 2005/0213100 A1 | 9/2005 | Murtagh et al. | |
| 2006/0170904 A1* | 8/2006 | Kuczynski | G01K 5/52 356/32 |
| 2008/0007727 A1* | 1/2008 | Okawa | G01N 21/9503 356/237.3 |
| 2008/0055583 A1* | 3/2008 | Lecomte | G01B 11/162 356/32 |
| 2008/0151219 A1* | 6/2008 | Maris | G01B 11/02 356/33 |
| 2008/0225267 A1* | 9/2008 | Murtagh | G01N 21/1717 356/32 |
| 2009/0033931 A1* | 2/2009 | Murtagh | G01N 21/1717 356/317 |
| 2009/0257058 A1* | 10/2009 | Urano | G01N 21/9503 356/364 |
| 2012/0007978 A1 | 1/2012 | Passek et al. | |
| 2013/0003050 A1 | 1/2013 | Zhu et al. | |
| 2013/0083305 A1* | 4/2013 | Wu | G02B 7/32 355/56 |

FOREIGN PATENT DOCUMENTS

| | | |
|---|---|---|
| IE | 83736 B1 | 12/2004 |
| IE | 83845 B1 | 3/2005 |
| IE | 83994 B1 | 9/2005 |
| IE | S84618 B2 | 6/2007 |
| IE | 84681 B1 | 9/2007 |
| IE | 84784 B1 | 1/2008 |
| IE | 20060777 A1 | 9/2008 |
| WO | 2004048945 A1 | 6/2004 |
| WO | 2004072629 A1 | 8/2004 |
| WO | 2006111942 A1 | 10/2006 |
| WO | 2007049259 A1 | 5/2007 |
| WO | 2007049260 A1 | 5/2007 |

OTHER PUBLICATIONS

H. Chouaib et al., Rapid photoreflectance spectroscopy for strained silicon metrology, Review of Scientific Instruments 79, 103106 (2008) pp. 103106-1-103106-3.

H. Chouaib et al., A micro-optical modulation spectroscopy technique for local strain measurement, Review of Scientific Instruments 82, 043901 (2011) pp. 043901-1-043901-6.

D Lowney et al., Investigation of strain induced effects in silicon wafers due to proximity rapid thermal processing using micro-Raman spectroscopy and synchrotron x-ray topography, Institute of Physics Publishing, Semiconductor Science and Technology, vol. 17 (2002), pp. 1081-1089.

* cited by examiner

AUTOMATED INLINE INSPECTION OF WAFER EDGE STRAIN PROFILES USING RAPID PHOTOREFLECTANCE SPECTROSCOPY

PRIORITY

The present application claims the benefit under 35 U.S.C. §119(e) of U.S. Provisional Application Ser. No. 61/982,196, filed Apr. 21, 2014, and U.S. Provisional Application Ser. No. 62/057,126, filed Sep. 29, 2014, both of which are incorporated herein by reference.

FIELD OF THE INVENTION

The present invention is directed generally toward photoreflectance (PR), and more particularly to PR for strain measurement in silicon wafers.

BACKGROUND

Photoreflectance (PR) and piezoreflectance (PzR) of substrates such as silicon-germanium (SiGe), gallium arsenide (GaAs), indium gallium sulfate (InGaS) exhibit a typical band gap of approximately 1.5 eV or 3.5 eV.

Rapid PR (RPR) spectroscopy requires the simultaneous detection of a small modulated reflectance ($\Delta R$) signal and a large time-invariant, unmodulated reflectance signal R, and the relation of the small modulated reflectance and unmodulated reflectance ($\Delta R/R$). Even at parts of the spectrum where it is significant, $\Delta R$ is relatively small compared to the unmodulated reflectance R, of the order of several to hundreds parts per million. Various sources of optical and electrical noises will be present and these dominate the $\Delta R$ signal. However, the $\Delta R$ signal is always present at the known modulation frequency and so methods of frequency-discriminating signal recovery are typically employed to detect a signal at this known frequency. Therefore, phase sensitive lock-in amplification was required for the measurement of the $\Delta R$ signal in PR spectroscopy and the measurement was to be made at different times for each wavelength, so that the $\Delta R/R$ spectrum was therefore generally recorded in a serial spectral mode. This limits the practical speed of the PR measurement and precludes its widespread industrial application in high-speed production line inspection of semiconductor wafers.

Strained silicon (sSi) refers to silicon in which strain is engineered locally in a device structure or globally across a wafer by a local or global stress to accelerate electrons, which allows manufacture of faster devices. Faster sSi transistors due to increased electron mobility and velocity have already been proven. As a result, the technology of strain engineering is being widely used to speed carrier mobility in transistor channels in order to increase the drive currents.

Globally sSi on a wafer comprises a very thin layer of single-crystal silicon strained by pseudomorphic growth up to a critical thickness on a relaxed $Si_xGe_{1-x}$ stressing layer of wider lattice constant dependent on the Ge mole fraction x.

In all global sSi technologies with one exception, the strain in the silicon is described as biaxial, the result of two effects, namely, the expansion of the silicon lattice due to the wider lattice constant of the relaxed $Si_{1-x}Ge_x$ layer, which is tensile stressing it, and the contraction of the silicon lattice in the vertical direction because of its behavior as a near-perfect Poisson solid. These two strain effects, hydrostatic tension, and uniaxial compression, will be presently shown to be mirrored by two competing effects in the electronic band structure in the vicinity of the $E_1$ critical point of silicon, whose combined effect is measurable by PR spectroscopy. Such a sSi layer can be transferred onto an $SiO_2$ buried oxide layer while retaining the strain to form a strained silicon-on-insulator (SSOI) wafer.

X-ray diffractometry (XRD) and Raman spectroscopy (RS) have been used for strain measurement in silicon. XRD suffers from excessive measurement time, and RS has poor resolution. Other optical inspection techniques look for slip-lines on the surface or cracks in the edge of silicon wafers. Optical inspection methods detect defects rather than measuring strain and are therefore unsuitable for identifying problems before defects occur, controlling strain sources, relating strain defects to specific process parameters, or managing strain levels in wafers.

Consequently, it would be advantageous if an apparatus existed that is suitable for directly measuring strain in a wafer production process in time to apply the measurements to prevent defects.

SUMMARY

Accordingly, the present invention is directed to a novel method and apparatus for directly measuring strain in a wafer production process in time to apply the measurements to prevent defects.

In at least one embodiment of the present disclosure, PR spectroscopy is used to measure strain at or near the edge of a wafer in a production process. The strain measurement is used to anticipate defects and make prospective corrections in later stages of the production process. In another embodiment, strain measurements are used to associate various production steps with defects to enhance later production processes.

It is to be understood that both the foregoing general description and the following detailed description are exemplary and explanatory only and are not restrictive of the invention claimed. The accompanying drawings, which are incorporated in and constitute a part of the specification, illustrate an embodiment of the invention and together with the general description, serve to explain the principles.

BRIEF DESCRIPTION OF THE DRAWINGS

The numerous advantages of the present invention may be better understood by those skilled in the art by reference to the accompanying figures in which.

DETAILED DESCRIPTION

Reference will now be made in detail to the subject matter disclosed, which is illustrated in the accompanying drawings. The scope of the invention is limited only by the claims; numerous alternatives, modifications and equivalents are encompassed. For the purpose of clarity, technical material that is known in the technical fields related to the embodiments has not been described in detail to avoid unnecessarily obscuring the description.

An understanding of embodiments of the present disclosure may be further illuminated by U.S. Pat. No. 7,623,228, U.S. Pat. No. 7,659,979, and U.S. Patent App. Pub. No. 2013/0003050, all of which are hereby incorporated by reference.

PR spectroscopy provides a useful alternative to XRD and RS to meet the requirements for a nondestructive in-line strain metrology tool. Rapid PR (RPR), and specifically micro RPR (μRPR), provides a measurement of strain in sSi with a high degree of accuracy in a sufficiently short time for application as an on-line production quality assurance tool.

Embodiments of the present invention measure local wafer strain and local/global strain profiles on and near the edge of a silicon wafer based on μRPR methods. Such measurements allow for monitoring and management of the resulting impact of wafer edge strain on process yield and health.

Rapid thermal processing (RTP) of silicon wafers can lead to various forms of residual strain in the wafers. For example, the silicon wafer and wafer carrier heat-up and cool-down at different rates. As a result, the contact points between the silicon wafer and the wafer carrier can cause a local thermal gradient in the wafer that results in a corresponding thermally induced local residual strain that remains after the wafer cooled. Under some conditions, the residual strain is local and on a microscopic scale can exceed the yield strength of silicon. This may result in lattice defects such as slip dislocations and micro-cracks. These defects are undesirable both in terms of device yield and process health. Slip dislocations may induce slip line defects in surface films that propagate with further processing and compromise yield. Micro-cracks can lead to wafer breakage during further processing that can damage expensive processing equipment and reduce process throughput.

Measurement of wafer strain at/near the wafer edge provides insight into the status of a wafer's slip dislocations or susceptibility to developing slip dislocations, strain-related micro-cracking or susceptibility to developing micro-cracks, and susceptibility to strain-related wafer breakage.

Figure 1:
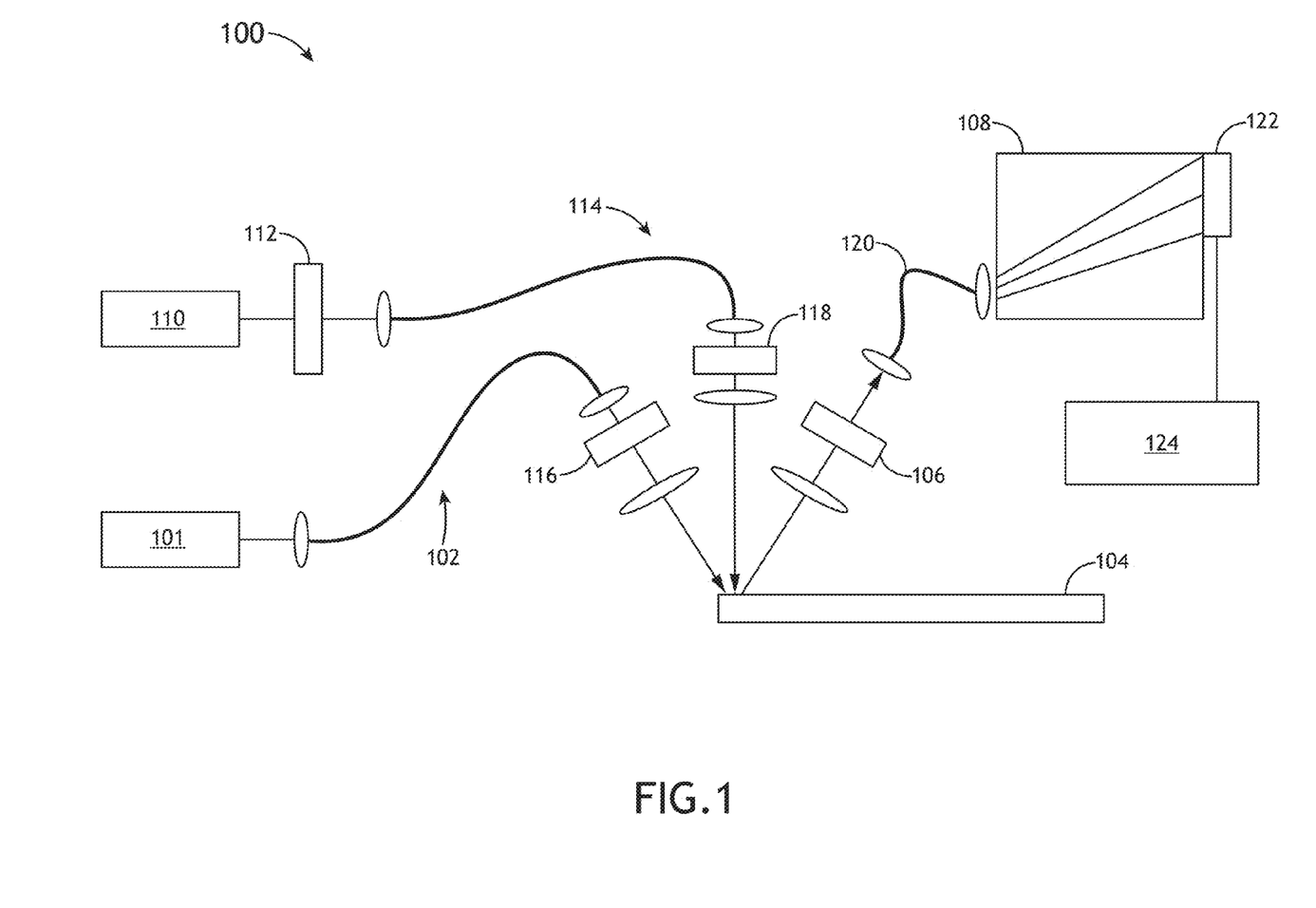
FIG. 1 shows a block diagram of a system according to one embodiment of the present invention for implementing RPR in a wafer fabrication process for edge strain measurement.

Referring to FIG. 1, a block diagram of a system 100 according to one embodiment of the present disclosure for implementing RPR in a wafer fabrication process for edge strain measurement is shown. In one embodiment, a probe light source 101 generates an incident probe beam and directs the incident beam through optical components 102, including fiber optics, onto an edge of a sample 104. In one embodiment, the incident light passes through an incident filter 116 to deliver a blue ultraviolet (UV) beam to the edge of the sample 104. Contemporaneously, a perturbation is optically applied to the edge of the sample 104 by a modulated pump beam. The modulated pump beam is produced by a pump laser 110, with the pump laser 110 beam passing through a modulator 112, such as a mechanical chopper, and modulated pump beam optical components 114 to the edge of the sample 104. In one embodiment, the modulated pump beam may be filtered by a pump beam filter 118 to a desirable frequency range. The reflectance of the edge of the sample 104 is altered by photoinjection of charge carriers via the interaction of the incident beam and modulated pump beam. In another embodiment, the modulated reflected incident beam may pass through a spectrograph filter 106 to filter the modulated reflected incident beam to a bandpass region of the spectrum in the region of the $E_1$ transition of silicon at approximately 3.4 eV. In another embodiment, the modulated reflected incident beam is transmitted through receiving optical components 120 and dispersed into its constituent wavelengths by a spectrograph 108 and the constituent components are sampled by a detector 122. In another embodiment, a processor 124 connected to the detector 122 analyzes the spectrographic data to measure wafer strain in-line in sSi wafers including SSOI and silicon-germanium on insulator by measuring the direct bandgap energy of the sSi layer and converting the value to strain using a theoretical model.

In another embodiment, the processor 124 reads the modulated reflectance $\Delta R$ signal as well as the unmodulated reflectance R signal from each pixel of the detector 122 in sufficiently rapid succession such that multiple measurements of the $\Delta R$ signal can be made within a single period of the modulation cycle. In this way, the system allows the simultaneous measurement of the PR signal at all wavelengths in parallel by means of multiplexing the readout. The acquisition time for the entire spectrum is approximately 1-2 ms (e.g., 1.03 ms). Depending on the measured structures, the acquisition may be averaged a plurality of times in order to improve the signal to noise ratio.

By way of example, in the case of a typical 200 Å top strained silicon layer thickness SSOI wafer, measured over the spectral range of the Si direct bandgap energy of 2.8 to 3.7 eV during a 10 s duration, and fitted to a summation of two low field PR line shapes, the RPR spectrum is modeled using an approximation based on the third derivative functional form, in which the critical point dimensionality is 2-d, and index parameter m=3, the RPR spectrum model may be defined by:

$$\frac{\Delta R}{R}_{PR}(E) = \mathrm{Re}\left[Ae^{i\theta}(E-E_g+i\Gamma)^{-3}\right]$$

It is noted that this model is appropriate given the negligible electro-optic effect and absence of Franz-Keldysh oscillations in the silicon PR spectra. Here, A is an amplitude factor, $\theta$ is a line shape phase factor, $E_g$ is the bandgap energy, and $\Gamma$ is the broadening energy parameter. The two transitions may be measured by fitting the RPR spectrum to correspond to the light hole (LH) and heavy hole (HH) direct bandgaps. It is noted that hydrostatic tensile strain may shift the interband transition (L band) energy, while compressive uniaxial strain along an axis normal to the wafer lifts the degeneracy of the valence band, leading to split LH and HH bands, and a splitting of the transition.

The behavior of the energy shift $\Delta E$ of the $E_1$ and associated transitions under hydrostatic strain and splitting in the energy shift due to uniaxial strain contribution have been described by a relationship based on extensive analysis of the electroreflectance response of silicon under uniaxial stress:

$$\Delta E = \sqrt{1/3}\,D_1^{\,1}(\epsilon_\perp + 2E_\parallel) \pm \sqrt{2/3}\,D_3^{\,3}(\epsilon_\perp + E_\parallel)$$

where the ± sign implies addition to obtain the shift in the HH and LH branches, $\epsilon_\perp$ is strain perpendicular to growth, $\epsilon_\parallel$ is strain in-plane, $D_1^{\,1}$ is the hydrostatic deformation potential, measured by Kondo and Moritani as −9.8 eV, and $D_3^{\,3}$ is the intraband strain deformation parameter along the direction perpendicular to growth, having a value of 4.7 eV. The relationship may therefore be rewritten as:

$$\Delta E = -5.658(\epsilon_\perp + 2\epsilon_\parallel) \pm 3.837(\epsilon_\perp + \epsilon_\parallel)$$

The strain tensor elements perpendicular to growth take the form:

$$\varepsilon_{xx} = \varepsilon_{yy} = \varepsilon_\parallel = \frac{a_0(Si_{1-x}Ge_x) - a_0(Si)}{a_0(Si)},$$

$$\varepsilon_{zz} = \varepsilon_\perp = -2\frac{C_{12}}{C_{11}}\varepsilon_\parallel,$$

$$\varepsilon_{xy} = \varepsilon_{xz} = \varepsilon_{yz} = 0$$

where x is the germanium concentration, $C_{11}$ and $C_{12}$ are the elastic constants, and the Bir-Pikus Hamiltonian for a G1 type band having the form:

$$a_0(Si_{1-x}Ge_x) = a_0(Si) + 0.200326x(1-x) + [a_0(Ge) - a_0(Si)]x^2$$

Therefore the lower energy branch of the split transition shifts according to:

$$\Delta E = E_{LH} - 3.4 = -0.1375\epsilon_\parallel (eV)$$

where $E_\parallel$ is expressed in percentage strain. As a result, the strain value is calculated using the bandgap shift of the $E_{LH}$ transition compared to the unstrained silicon direct bandgap 3.4 eV. It is conventional to quote the tensile strain in the plane of the wafer.

RPR results may be compared to RS. Actual calibration against a range of RS values gives a calibration result of 3.399 and −0.1368 eV as unstrained silicon bandgap and conversion factor, respectively.

PR techniques may be used to measure tensile in-plane edge strain in biaxially strained SSOI wafers. A decrease in the acquisition time by a factor of 100 to 500 may be achieved for a nondestructive technique suitable for in-line sSi metrology. A decrease and split ($E_{LH}$ and $E_{HH}$) in the silicon bandgap have been observed upon tensile strain. Based on theoretical models, the $E_{LH}$ transition value may be converted to biaxial tensile strain, which is consistent with RS results.

Figure 2:
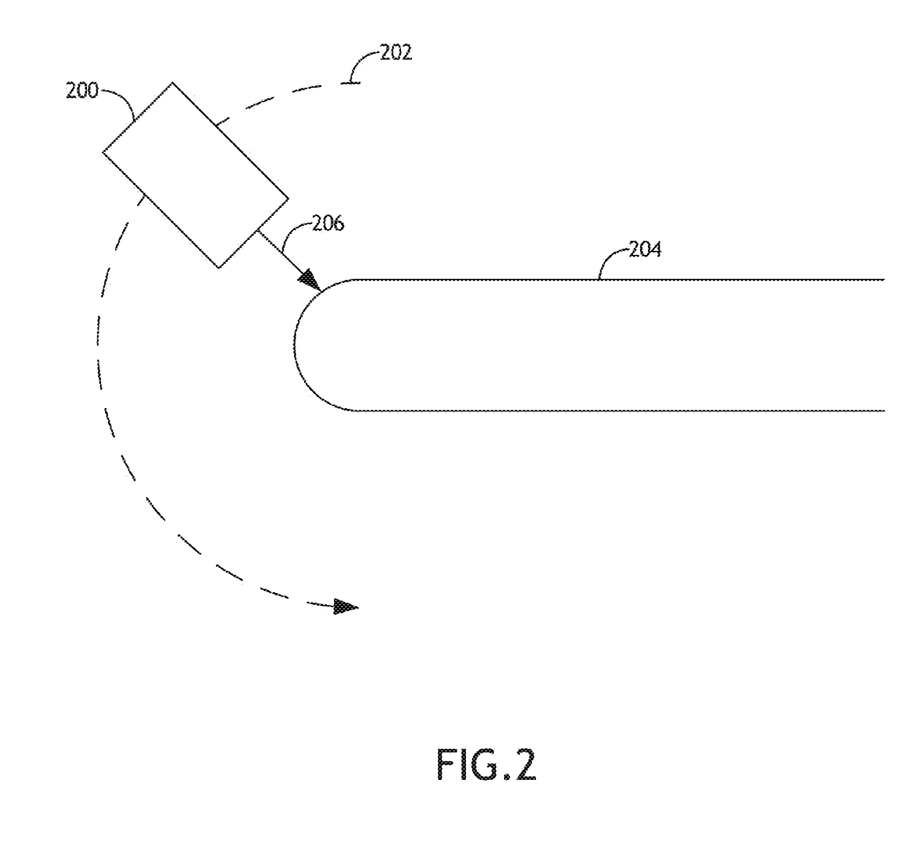
FIG. 2 shows an environmental representation of one embodiment of the present invention.

Referring to FIG. 2, an environmental representation of one embodiment of the present disclosure is shown. In one embodiment, strain measurements taken at or near the edge of a wafer 224 are made with an optical scanning system 200 as described herein. In another embodiment, the optical axis 206 of the optical scanning system 200 is maintained substantially normal to the portion of the surface of the wafer 202 where the measurement is made. In addition, the portion of the surface of the wafer 204 where the measurement is made is maintained substantially at the optimal focus position of the optical scanning system 200 throughout the entire trajectory 202 traveled by the optical scanning system 200. It is noted that maintain optimal (or adequate) focus may be accomplished using the optically measured wafer edge profiles for feed-forward to wafer r and z stages or any other metrics necessary to maintain focus and normality of the optical axis 206 even where the edge is irregular.

The feed-forward procedure may be combined with a real-time auto-focus mechanism to mitigate errors in the measurement of the wafer 204 edge profile. Alternatively, the feed-forward procedure may be replaced with a combined real-time auto-focus mechanism and default wafer profile. For example, a semi-circle or other pattern may be used for the wafer edge profile.

Figure 3:
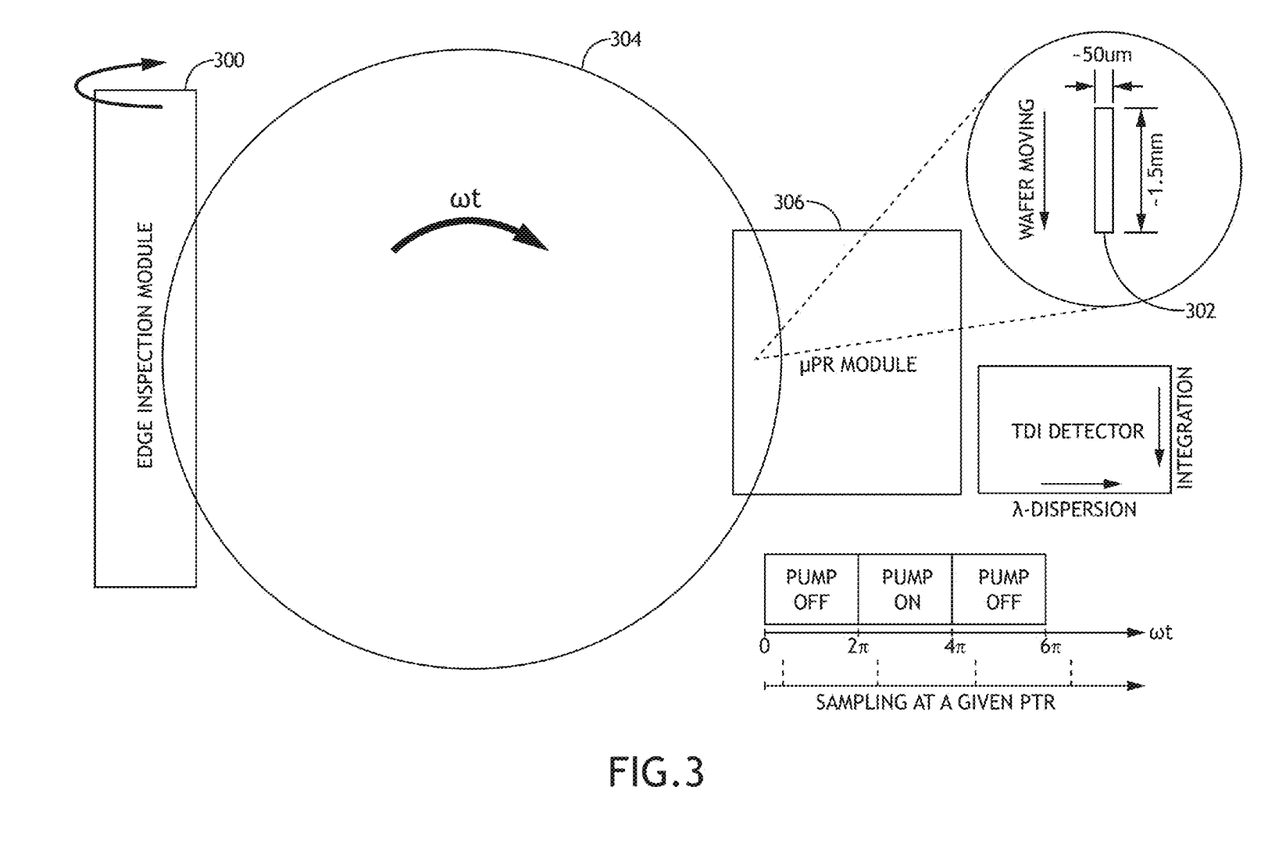
FIG. 3 shows an environmental representation of one embodiment of the present invention.

Referring to FIG. 3, an environmental representation of one embodiment of the present invention is shown. In one embodiment, a wafer 304 in a production process may be inspected by various inspection modules 300, 306. In one embodiment, module 300 includes an edge inspection module. In another embodiment, module 306 includes a μRPR edge strain measurement module 306. In one embodiment, the μRPR strain measurement module 306 may measure strain at sample spot sizes 302 of several millimeters down to less than 10 micro-meters. In another embodiment, the μRPR strain measurement module 306 may sample wafer 304 edge locations as the wafer 304 moves. Alternatively, the μRPR strain measurement module 306 may take measurements in a continuous fashion, repeatedly, over a track defined by an edge profile. Multiple tracks may be measured serially or in in parallel. The μRPR edge strain measurement module 306 may include a time-delay integration (TDI) sensor for performing the actual image collection. Furthermore, because the μRPR strain measurement module 306 collects both modulated and unmodulated light reflected from the wafer 304, a modulating pump beam source may be periodically turned on and off to modulate an incident beam at a given sampling rate.

It is noted that the μRPR optics head may provide for multiple simultaneous measurement points as a means to increase throughput and mitigate laser damage. In one embodiment, the μRPR optics head may be on a dedicated wafer inspection system, or may be integrated into a wafer inspection platform with multiple inspection systems. In another embodiment, the μRPR may be mounted such that a step-wise or continuous measurement is made of a specific zone circumference of the wafer.

Figure 4:
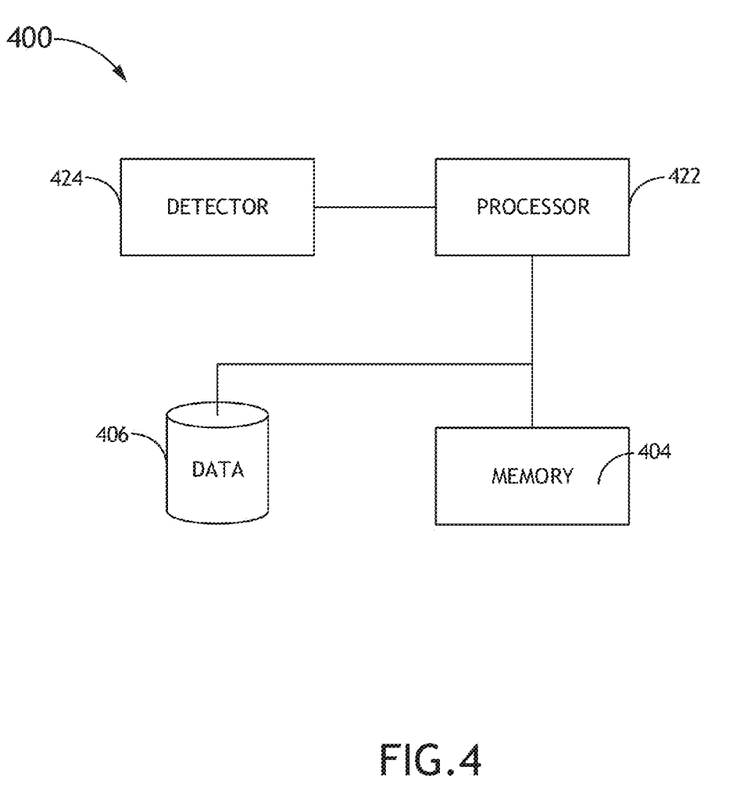
FIG. 4 shows a block diagram for a computer system according to one embodiment of the present invention.

Referring to FIG. 4, a block diagram for a computer system according to one embodiment of the present invention is shown. In one embodiment, the computer system 400 includes a processor 422, memory 404 connected to the processor 422 for storing computer executable code, and a data storage element 406 for storing wafer profile data. In another embodiment, a spectral detector 424, such as a TDI sensor, is connected to the processor 422 to receive reflected light from the edge of a wafer and modulated reflected light from the edge of the wafer via a spectrograph.

In a wafer production process, the edge of a spinning wafer may be inspected for strain. In one embodiment, an illumination device may provide an incident beam arranged to illuminate a portion of the wafer. The incident beam is then reflected to a spectrograph for detection by the spectral detector 424. In another embodiment, the illumination device may also include a pump laser to produce a modulation beam that illuminates the portion of the wafer to produce a modulated incident beam reflected to the spectrograph for detection by the spectral detector 424.

In one embodiment, the processor 422 receives spectral data and produces a strain measurement associated with the illuminated portion of the wafer, the illuminated portion being a surface on the or about the edge of the wafer. In another embodiment, the processor 422 may adjust the location and orientation of the spectral detector 424 based on an edge profile stored in the data storage element 406, or a predetermined spot locations where strain measurements are desirable. Based on the strain measurements, the processor 422 may determine that a defect is likely in the production process or that a strain threshold for a portion of the wafer has been reached. Furthermore, given known production process parameters, the processor 422 may determine that strain related defects in the edge of a wafer may be correlated to such parameters; for example, temperature disparities during the production process.

Local and global strain profiles on or near a wafer edge may allow the processor 422 to identify problematic stain profiles before defects or micro-cracks appear, or at least identify wafers that may already have developed strain-related defects; control strain-related defects such as slip lines and micro-cracks at or near the edge of the wafer; identify and control strain sources; and manage strain level in wafers.

Multiple μRPR strain measurements can be made on a wafer in a stepwise or continuous fashion about the circumference of the wafer. For example, measurements may be made of a top edge surface, bottom edge surface, and side surface of an edge of the wafer, and may incorporate care areas and/or exclusion zones for the measurement. Multiple μRPR strain measurements may be post-processed to generate a continuous strain profile at virtually any scale; e.g. globally such as around the circumference of the top edge, side edge, and bottom edge of the wafer down to a local region whose smallest size is limited by the sample spot size.

Figure 5:
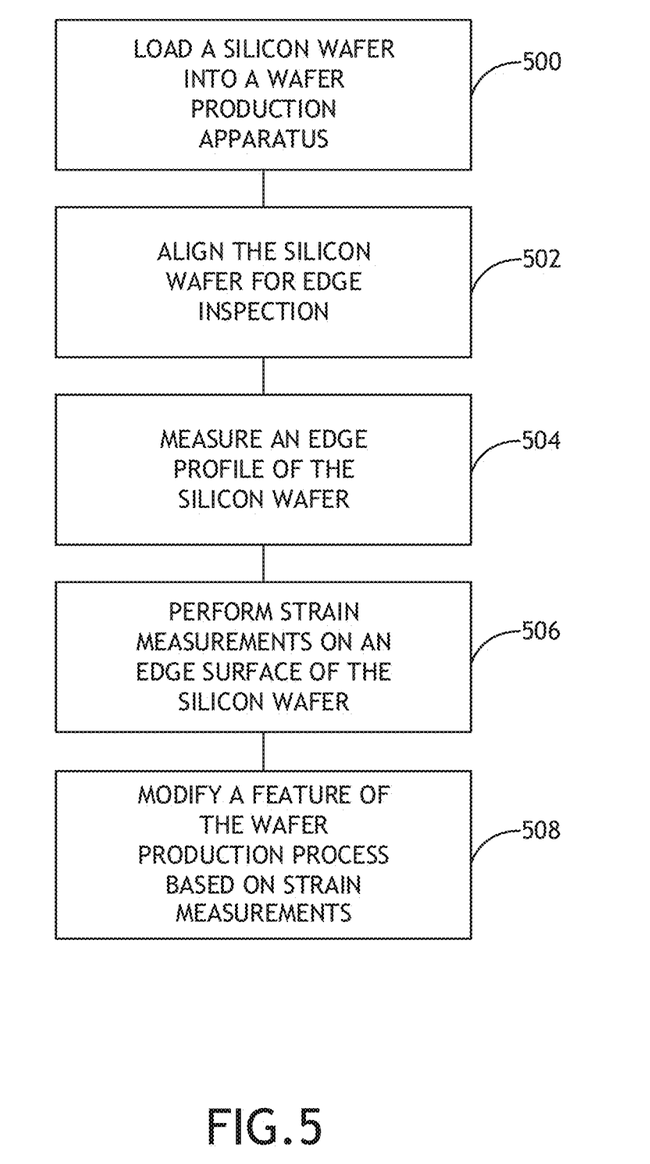
FIG. 5 shows a flowchart of a method for edge strain measurement.

Referring to FIG. 5, a flowchart depicting a method for edge strain measurement is shown. In a first step 500, a wafer (e.g., silicon wafer) is loaded into a wafer production apparatus. For example, the production apparatus may include, but is not limited to, an embodiment of the present disclosure. In a second step 502, the wafer is aligned for edge inspection. In a third step, the wafer production apparatus then measures 504 an edge profile of the wafer. In a fourth step 506, the wafer production apparatus performs a strain measurement on an edge surface of the wafer. For example, the measurements may include, but are not limited to, spot measurements or continuous measurements. In another embodiment, the wafer production apparatus may track multiple parameters when performing the strain measurements; such parameters may include identifying particular areas of interest for spot measurement, particular areas identified via previous production processes that are prone to strain related defects, monitoring strain values for a predetermined threshold, or SNR parameters. In a fifth step 508, the wafer production apparatus may modifies a feature of the wafer production process based on the edge strain measurements.

Embodiments of the present disclosure may have an edge strain measurement resolution of better than 0.1%, a silicon yield stress of approximately 1 GPa at room temperature and approximately 10 GPa at 1000° C., and a Young's modulus of approximately 130.

Figure 6:
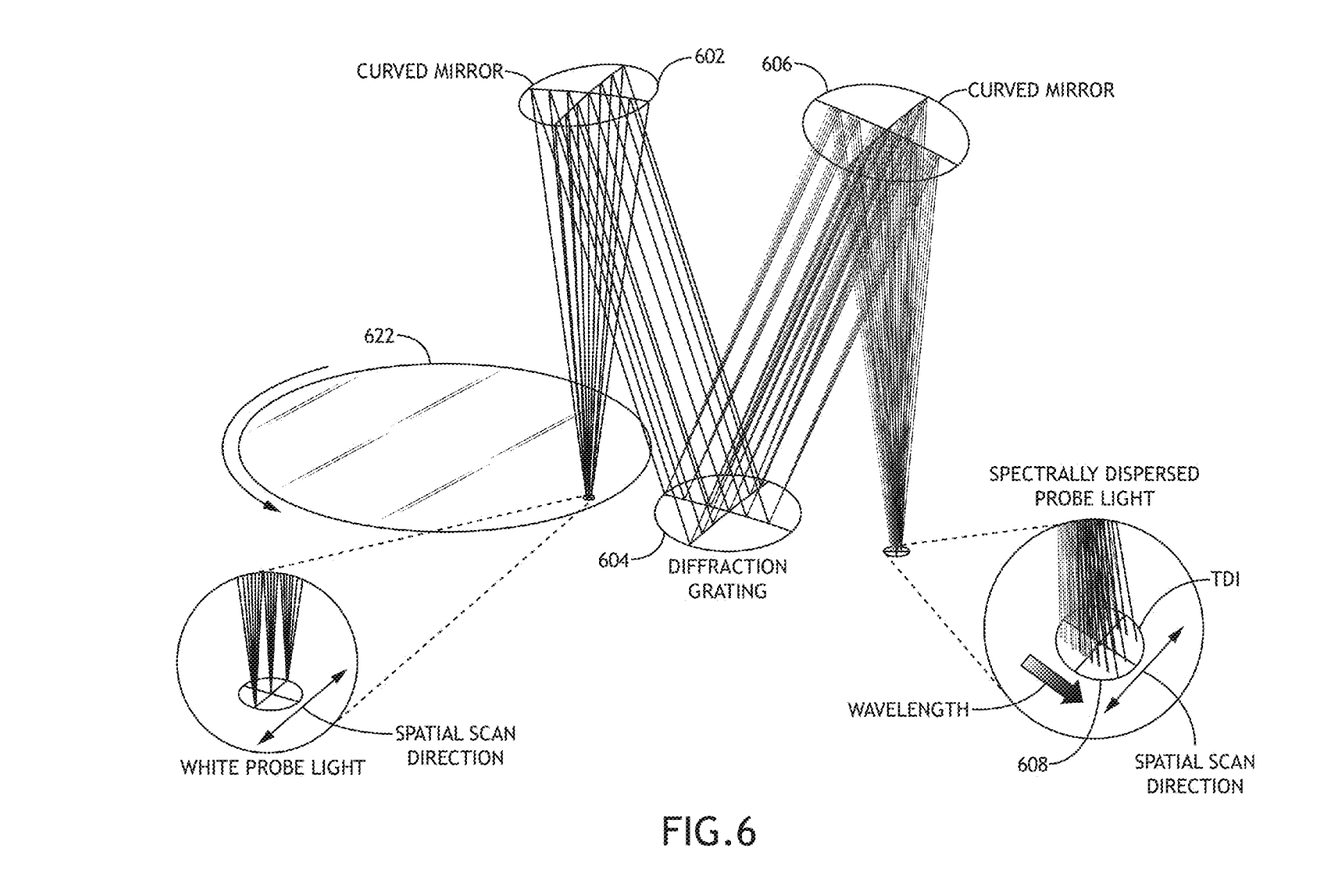
FIG. 6 shows optical elements in an embodiment of the present invention.

Referring to FIG. 6, optical elements of an embodiment of the present disclosure are shown. In one embodiment, the edge of a spinning wafer 622 in a wafer production process is illuminated. For example, as shown in FIG. 6, a white probe light may illuminate the wafer and scan the wafer along a selected spatial scan direction. In another embodiment, the reflected illuminated light may be collimated by a first curved mirror 602 and reflected onto a diffraction grating 604. In one embodiment, the diffraction grating 604 reflects a diffracted image from the edge of the spinning wafer 622 to a second curved mirror 606 that focuses the diffracted image onto a TDI sensor 608. As shown in FIG. 6, light received by the TDI sensor 608 may be across the sensor as a function of wavelength, with the scanning direction being arranged orthogonal to this direction. In another embodiment, data from the TDI sensor 608 is used to determine a strain measurement associated with the edge of the spinning wafer 622.

Figure 7:
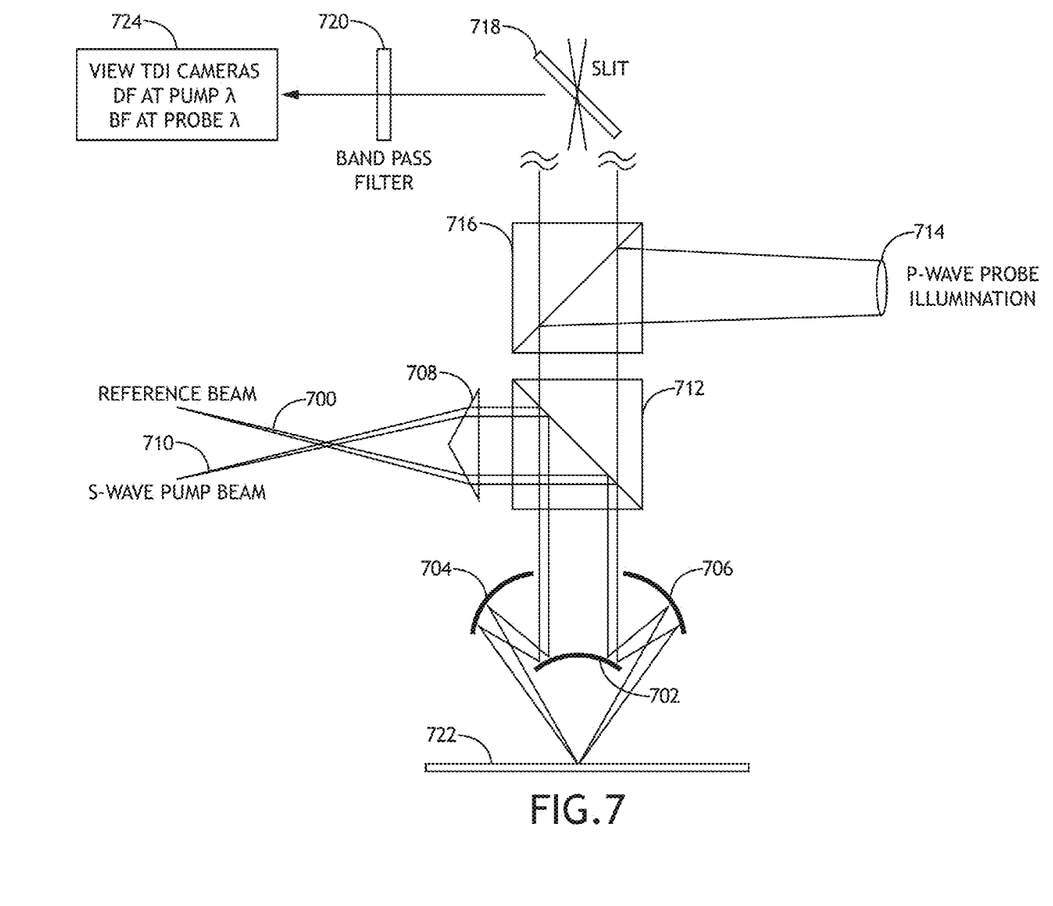
FIG. 7 shows a block diagram according to another embodiment of the present invention for implementing RPR in a wafer fabrication process.

Referring to FIG. 7, a block diagram according to another embodiment of the present disclosure for implementing RPR in a wafer fabrication process is shown. In one embodiment, a reference beam 700, such as a reference laser beam (e.g., reference laser suitable for AF), passes through optical elements 702, 704, 706, 708, 712 to the edge of a wafer 722. Contemporaneously, a pump beam 710, such as an S-wave pump beam, passes through the same optical elements 702, 704, 706, 708, 712 to the same spot on the edge of the wafer 722.

In one embodiment, optical element 708 includes one or more prisms 708 (e.g., beam separation prism) for directing the reference beam 700 and pump beam 710 along a common entrance path. In another embodiment, optical element 712 includes a first beam splitter 712 (e.g., polarized beam splitter or GLAN-type beam splitter) for reflecting the reference beam 700 and pump beam 710 to a first mirror 702.

For example, the first mirror 702 may be, but is not required to be, a convex mirror for reflecting the reference beam 700 and pump beam 710 to a second mirror 704 and third mirror 706 respectively. By way of another example, the second mirror 704 and third mirror 706 may be, but are not required to be, concave mirrors for focusing the reference beam 700 and pump beam 710 to a particular portion of the edge of the wafer 722. In another embodiment, the second mirror 704 and third mirror 706 may be arranged so as to focus the reference beam 700 and pump beam 710 onto the wafer 722 from different angles.

In at least one embodiment, a P-wave illuminator 714 may introduce a probe beam to a second beam splitter 716 (e.g., 50/50 beam splitter), which directs a portion of the probe beam through one or more optical elements 702, 704, 706, 712 to combine with the reference beam 700 and pump beam 710.

In another embodiment, light reflected from the wafer 722 traverses one or more of the optical elements 702, 704, 706 through the first beam splitter 712 and the second beam splitter 716 to a detector 724. In at least one embodiment, a slit diffraction element 718 (e.g., slight has long width aligned with TDI) and a band-pass filter 720 may be interposed between the second beam splitter 716 and the TDI detector 724.

Embodiments of the present invention provide a means to measure and control wafer edge strain, in-line, before associated defects and adverse consequences occur as described.

It is believed that the present invention and many of its attendant advantages will be understood by the foregoing description of embodiments of the present invention, and it will be apparent that various changes may be made in the form, construction, and arrangement of the components thereof without departing from the scope and spirit of the invention or without sacrificing all of its material advantages. The form herein before described being merely an explanatory embodiment thereof, it is the intention of the following claims to encompass and include such changes.

What is claimed is:

1. A system for measuring edge strain in a wafer production process comprising:
    a processor;
    a wafer illuminating device comprising:
        an incident probe light source configured to illuminate a portion of a wafer; and
        a pump light source configured to modulate a portion of light from the incident light source reflected off the portion of the wafer;
    a spectrograph configured to receive a reflected beam from the wafer illumination device via the wafer; and
    a light detector connected to the processor and configured for receiving light from the spectrograph,
    wherein:

the wafer illumination device is configured to illuminate an edge of a wafer; and the processor is configured to:
determine a strain value based on data received from the light detector; and
identify one or more slip dislocations based on the strain value at the edge of the wafer.

2. The system of claim 1, wherein:
the wafer illumination device is configured to traverse a path such that an axis defined by the wafer illumination device and the portion of the wafer being illuminated is orthogonal to a tangent of the edge of the wafer over the entire path; and
the processor is configured to control a position and orientation of the wafer illumination device along the path.

3. The system of claim 1, wherein the processor is configured to correlate the strain value to one or more wafer production parameters.

4. The system of claim 3, wherein the processor is configured to:
identify a wafer defect; and
correlate the strain value to the identified wafer defect and the one or more wafer production parameters.

5. The system of claim 1, wherein the processor is configured to correlate the strain value to an anticipated wafer defect.

6. The system of claim 1, wherein the processor is configured to compare the strain value to a threshold wafer strain value.

7. The system of claim 1, wherein the processor is configured to:
identify a wafer defect; and
correlate the strain value to the identified wafer defect.

8. The system of claim 1, wherein at least one of the incident light source or the pump light source is a laser.

9. A computer apparatus comprising:
a processor;
a wafer illuminating device connected to the processor, comprising:
an incident probe light source configured to illuminate a portion of a wafer; and
a pump light source configured to modulate a portion of light from the incident light source reflected off the portion of the wafer;
a spectrograph configured to receive a reflected beam from the wafer illumination device via the wafer; and
a light detector connected to the processor configured for detecting spectrographic data from the spectrograph; and
memory connected to the processor for storing computer executable code,
wherein the computer executable code is configured to instruct the processor to:
receive spectrographic data corresponding to a portion of a wafer edge;
determine a strain value based on the spectrographic data; and
identify one or more slip dislocations based on the strain value at the edge of the wafer.

10. The computer apparatus of claim 9, wherein the computer executable code is configured to instruct the processor to orient the wafer illumination device to illuminate the portion of the wafer edge.

11. The computer apparatus of claim 9, wherein the computer executable code is configured to instruct the processor to correlate the strain value to one or more wafer production parameters.

12. The computer apparatus of claim 11, wherein the computer executable code is configured to instruct the processor to:
identify a wafer defect; and
correlate the strain value to the identified wafer defect and the one or more wafer production parameters.

13. The computer apparatus of claim 9, wherein the computer executable code is configured to instruct the processor to correlate the strain value to an anticipated wafer defect.

14. The computer apparatus of claim 9, wherein the computer executable code is configured to instruct the processor to compare the strain value to a threshold wafer strain value.

15. The computer apparatus of claim 9, wherein the computer executable code is configured to instruct the processor to:
identify a wafer defect; and
correlate the strain value to the identified wafer defect.

16. A method for measuring strain at a wafer edge in a wafer production process comprising:
producing, with a wafer inspection apparatus, an edge profile of a wafer in a wafer production process;
illuminating, with a wafer illumination device, an edge of the wafer;
receiving, with a processor, spectrographic data corresponding to the edge of the wafer;
determining, with the processor, a strain value based on the spectrographic data;
identifying one or more slip dislocations based on the strain value at the edge of the wafer; and
modifying a feature of the wafer production process based on the strain value.

17. The method of claim 16, further comprising correlating the strain value to one or more wafer production parameters.

18. The method of claim 17, further comprising
identifying a wafer defect; and
correlating the strain value to the identified wafer defect and the one or more wafer production parameters.

19. The method of claim 16, further comprising correlating the strain value to an anticipated wafer defect.

20. The method of claim 16, further comprising comparing the strain value to a threshold wafer strain value.

21. The method of claim 16, further comprising identifying a portion of the edge profile to be excluded from illumination.

* * * * *